United States Patent [19]
Halvorson et al.

[11] Patent Number: 5,874,392
[45] Date of Patent: Feb. 23, 1999

[54] SOAP

[76] Inventors: Raymond George Halvorson; Elaine Melody Halvorson, both of #22—32705 Fraser Crescent, Mission, British Columbia, Canada, V2V 1C9

[21] Appl. No.: 852,488

[22] Filed: May 7, 1997

[51] Int. Cl.$^6$ ............................. C11D 9/26; C11D 17/00; A61K 7/50

[52] U.S. Cl. ..................... 510/129; 510/152; 510/153; 510/458

[58] Field of Search ..................................... 510/140, 141, 510/150, 151, 152, 153, 129, 458

[56] References Cited

U.S. PATENT DOCUMENTS

| | | | |
|---|---|---|---|
| 4,767,560 | 8/1988 | Gervasio | 252/108 |
| 4,812,253 | 3/1989 | Small et al. | 252/132 |
| 4,861,507 | 8/1989 | Gervasio | 252/108 |
| 5,705,462 | 1/1998 | Hormes et al. | 510/141 |
| 5,712,235 | 1/1998 | Nieendick et al. | 510/151 |
| 5,750,481 | 5/1998 | Del Vecchio et al. | 510/152 |

*Primary Examiner*—Paul Lieberman
*Assistant Examiner*—Necholus Ogden
*Attorney, Agent, or Firm*—Bull, Housser & Tupper

[57] ABSTRACT

The invention provides a multi purpose soap bar which can be used for cleaning the human body and shampooing and conditioning the hair consisting of the following ingredients in the volume % as specified:

| | |
|---|---|
| Caproic Acid | 0.10–0.26 |
| Caprylic Acid | 1.41–3.48 |
| Capric Acid | 1.00–2.48 |
| Lauric Acid | 7.0–17.4 |
| Myristic Acid | 2.47–6.7 |
| Palmitic Acid | 1.21–31.7 |
| Stearic Acid | 0.15–14.5 |
| Oleic Acid | 1.3–57.1 |
| Linoleic Acid | 0.31–19.2 |
| Linolenic Acid | 0.01–4.8 |
| Alpha Linoleic Acid | 0.0–0.7 |
| Vitamin E | 0.0–3.6 |
| Water/Sodium Hydroxide Mixed 3:1 | 27.0–27.2 |
| Honey | 0.0–1.0 |
| Citric Acid | 0–0.4 |
| Lecithin | 0–0.2 |
| Palmitoleic Acid | 0–0.11 |
| Erucic Acid | 0–0.65 |
| Arachidic Acid | 0–.29 |

23 Claims, No Drawings

SOAP

BACKGROUND OF THE INVENTION

The invention relates to a multi purpose soap bar that can be used for cleaning the human body and shampooing and conditioning the hair The term "conditioning" refers to a process to reduce chances of tangling or clumping of the hair after the hair has been washed, as well as providing the hair with nourishment.

In the past, the basic ingredient of soap was animal fat or tallow with wood ash based lye used in the saponification process. Ideally a bar of soap is of suitable hardness to maximize user cycles and resistance to water reabsorption when not in use, while at the same time providing sufficient lather to enhance the cleaning ability of the soap. Animal fat or tallow as the active ingredient in the soap making process will generally meet these user demands to a greater or lesser degree. Current soap production continues to rely heavily on animal fats in their products to meet consumer demand and production requirements. In addition, various synthetic compounds and mixtures of compounds have become very popular additions in modem soap making technology to improve soap quality and user satisfaction. However, animal fat and synthetic based soaps are generally resistant to the natural breakdown processes (i.e. biodegradability) and are thus relatively persistent in the environment.

In most cases soap is used solely for a single purpose, that is as a hygienic skin cleansing agent. Bar soap is generally unsuitable as a hair shampoo and/or conditioner as bar soap can leave an undesireable residue on the hair which is difficult to rinse out, generally provides insufficient cleaning of the hair and can leave hair difficult to manage and dried out particularly after repeated use.

Over the years attempts have been made to develop a hard soap bar having acceptable hair cleansing characteristics, primarily through the use of various synthetic components. One such soap bar is described in U.S. Pat. No. 4,012,341 (Orshitzer). The Orshitzer patent provides a asynthetic all detergent shampoo bar in which a mixture of an anionic and non-ionic detergent together with a fatty acid monoethanolamide, preferably the stearic acid, comprise the primary active ingredients. These ingredients are relatively non-biodegradable and, once used by consumers, will persist in the environment.

There is a need for a hard soap bar which:
1. is produced using readily biodegradable natural all vegetable oils and containing no animal products, manufactured chemicals or synthetic compounds
2. provides a copious satisfying lather in a variety of water conditions
3. leaves the skin soft and smooth and adequately cleansed; and
4. possess necessary hair cleansing and hair conditioning qualities.

Such a soap bar would permit use and transport of hair shampoo and conditioner in a solid form, obviating the need for separate liquid shampoo and the resultant problems associated with transporting liquid shampoo and disposing of liquid shampoo containers. Consumers can use the hard soap bar for both skin cleansing and for hair cleansing and conditioning.

SUMMARY OF THE INVENTION

The invention provides a hard soap bar that can be used for cleaning the body, shampooing the hair and conditioning the hair, all in one bar. In addition, the soap bar is composed of vegetable oil with no animal products, is effective in water of wide-ranging pH levels, hardness, salinity or temperatures and is biodegradable and thus is environmentally safe. In addition, the soap is non-irritating on sensitive body parts, provides excellent cleansing capabilities both on the skin and in the hair, provides excellent hair conditioning capabilities and most embodiments produce generous lather. The hard soap bar of this invention may be packaged in paper, cardboard or like recyclable material and may be transported in its solid form. The soap bar is particularly advantageous for outdoor and wilderness use and also in other applications where an easily transportable multi-use bar suitable for skin cleansing and hair shampooing and conditioning applications is required.

In one embodiment of the invention a multi use soap bar for skin and hair cleansing includes the following ingredients:

| | |
|---|---|
| Caproic Acid | 0.10–0.26 |
| Caprylic Acid | 1.41–3.48 |
| Capric Acid | 1.00–2.48 |
| Lauric Acid | 7.0–17.4 |
| Myristic Acid | 2.47–6.7 |
| Palmitic Acid | 1.21–31.7 |
| Stearic Acid | 0.15–14.5 |
| Oleic Acid | 1.3–57.1 |
| Linoleic Acid | 0.31–19.2 |
| Linolenic Acid | 0.01–4.8 |
| Alpha Linoleic Acid | 0.0–0.7 |
| Vitamin E | 0.0–3.6 |
| Water/Sodium Hydroxide Mixed 3:1 | 27.0–27.2 |
| Honey | 0.0–1.0 |
| Citric Acid | 0–0.4 |
| Lecithin | 0–0.2 |
| Palmitoleic Acid | 0–0.11 |
| Erucic Acid | 0–0.65 |
| Arachidic Acid | 0.29 |

In a further embodiment of the invention the cleansing bar includes the following ingredients:

| | |
|---|---|
| Caproic Acid | 0.125–0.25 |
| Caprylic Acid | 1.7–3.4 |
| Capric Acid | 1.2–2.4 |
| Lauric Acid | 8.5–17.0 |
| Myristic Acid | 3.3–6.2 |
| Palmitic Acid | 4.2–19.8 |
| Stearic Acid | 2.1–6.1 |
| Oleic Acid | 13.2–28.6 |
| Linoleic Acid | 3.0–11.4 |
| Linolenic Acid | 0.3–5.0 |
| Alpha Linoleic Acid | 0.025–0.16 |
| Vitamin E | 0.126–0.79 |
| Water/Sodium Hydroxide Mixed 3:1 | 27.10 |
| Honey | 0.38 |
| Citric Acid | 0.18 |
| Lecithin | 0.09 |

In a further embodiment of the invention a skin and hair cleansing bar as provided including the following ingredients:

| Ingredient | Volume % |
|---|---|
| Water/Sodium Hydroxide Mixed 3:1 | 27–27.2 |
| Coconut Oil | 15–37 |
| Olive Oil | 0–3 |
| Wheat Germ Oil | 0–10 |
| Honey | 0–1 |
| Citric Acid | 0–0.4 |
| Lecithin | 0–0.2 |

DETAILED DISCLOSURE

The invention is susceptible of expression in several different mixtures or embodiments, which utilize a wide variety of vegetable oils with a few additional substances in relatively small quantities. However, all examples of the invention utilize the following ingredients, in an amount no less than the minimum amount stipulated below.

All mixtures herein are expressed as percentages by volume.

| Minimum Ingredients | | |
|---|---|---|
| A. | Purified or Distilled water/Sodium/Hydroxide mixed 3:1 | 27.1 |
| B. | Coconut Oil | 36.1 |
| C. | Hydrogenated Vegetable Oil chosen from Hyd. Canola Oil or Hyd. Palm Oil or a mixture of each | 11.9 |
| D. | Wheat Germ Oil | 2.3 |
| E. | Canola Oil or Palm Oil* | 19.7 |
| F. | Honey | 0.2 |
| G. | Citric Acid | 0.2 |

Possible Substitutes
1. If Hydrogenated Canola Oil is used for ingredient C, then Palm Oil will be used for ingredient E.
2. If Hydrogenated palm oil is used for ingredient C, then Canola Oil will be used for ingredient E.
3. If a mixture of Hydrogenated Canola Oil and Hydrogenated Palm Oil is used for ingredient C, then equal and opposite proportions of Palm Oil and Canola oil will be used for ingredient E.

In several examples following the main ingredients comprise seven vegetable oils which are termed "basic components" which have specific chemical compositions as below.

| BASIC COMPONENTS | | | |
|---|---|---|---|
| Common Name | Chemical Name | | |
| Coconut Oil | Caproic Acid | C6:0 | 0.7% |
| | Caprylic Acid | C8:0 | 9.4% |
| | Capric Acid | C10:0 | 6.7% |
| | Lauric Acid | C12:0 | 46.7% |
| | Myristic Acid | C14:0 | 16.5% |
| | Palmitic Acid | C16:0 | 8.1% |
| | Stearic Acid | C18:0 | 1.0% |
| | Oleic Acid | C18:1 | 8.7% |
| | Linoleic Acid | C18:2 | 2.1% |
| | Linolenic Acid | C18:3 | 0.1% |
| Hydrogenated Palm Oil | Lauric Acid | C12:0 | 0.6% |
| | Myristic Acid | C14:0 | 1.4% |
| | Palmitic Acid | C16:0 | 56% |
| | Stearic Acid | C18:0 | 39% |
| | Oleic Acid | C18:1 | 3% |
| Olive Oil | Palmitic Acid | C16:0 | 8% |
| | Stearic Acid | C18:0 | 2% |
| | Oleic Acid | C18:1 | 82% |
| | Linoleic Acid | C18:2 | 8% |
| Canola Oil | Palmitic Acid | C16:0 | 3–4.5% |
| | Palmitoleic Acid | C16:1 | 0.2–0.3% |
| | Stearic Acid | C18:0 | 1.3–1.7% |
| | Oleic Acid | C18:1 | 56–62% |
| | Linoleic Acid | C18:2 | 19–24% |
| | Linolenic Acid | C18:3 | 8.2–13% |
| | Erucic Acid | C22:1 | 0.2–1.8% |
| Hydrogenated Canola Oil | Palmitic Acid | C16:0 | 4.5% |
| | Stearic Acid | C18:1 | 24.11% |
| | Arachidic Acid | C20:0 | 0.92% |
| | Oleic Acid | C18:1 | 69.29% |
| | Linoleic Acid | C18:2 | 0.69% |
| | Linolenic Acid | C18:3 | 0.49% |
| Palm Oil | Lauric Acid | C12:0 | 1% |
| | Myristic Acid | C14:0 | 1.0% |
| | Palmitic Acid | C16:0 | 44% |
| | Stearic Acid | C18:0 | 4.4% |
| | Oleic Acid | C18:1 | 39.9% |
| | Linoleic Acid | C18:2 | 10.3% |
| | Arachidic Acid | C20:0 | 0.3% |

| -continued | | | |
|---|---|---|---|
| Wheat Germ Oil | Vitamin E | | 36% |
| (Triticum Aestivum Oleum) | Linoleic Acid | C18:2 | 57% |
| | Alpha Linoleic Acid | C18:3 | 7% |

Other basic components comprise:

Sodium Hydroxide flakes
Purified or Distilled Water ($H_2O$)
Liquid Unpasturized Honey
Citric Acid powder
Liquid Lecithin
Scent (perfume oil or essential oil of choice)

SUPPLIERS

Coconut Oil Omega Nutrition, Vancouver, B.C.

Hydrogenated Palm Oil Premier Edible Oil Corp., Portland, Oreg.

Olive Oil Spectrum Naturals Inc., Petaluma, Calif.

Canola Oil Spectrum Naturals Inc., Petaluma, Calif.

Hydrogenated Canola Oil Canamera Foods, Edmonton, AB

Palm Oil Omega Nutrition, Vancouver, B.C.

Optimum oils in liquid state are cold-pressed natural oils. However, other brands and forms of oils may be used with satisfactory results.

Purified or distilled water gives equally consistent results. Tap water may be too hard or too soft and will affect saponification. If water is too soft, soap will be brittle and harsh. If water is too hard, soap will not saponify completely as some of the sodium hydroxide is used to soften the water.

PREFERRED EMBODIMENT

| | |
|---|---|
| Caproic Acid | 0.25 |
| Caprylic Acid | 3.4 |
| Capric Acid | 2.4 |
| Lauric Acid | 17.0 |
| Myristic Acid | 6.0 |
| Palmitic Acid | 10.3–10.7 |
| Stearic Acid | 5.3–5.4 |
| Oleic Acid | 16.4–17.6 |
| Linoleic Acid | 4.8–5.4 |
| Linolenic Acid | 2.9–3.9 |
| Palmitoleic Acid | 0.04–0.06 |
| Erucic Acid | 0.04–0.35 |
| Alpha Linoleic Acid | 0.16 |
| Vitamin E | 0.79 |
| Water/Sodium Hydroxide mixed 3/1 | 27.10 |
| Honey | 0.38 |
| Citric Acid | 0.18 |
| Lecithin | 0.09 |

This embodiment is made from a mixture of the following ingredients:

| | |
|---|---|
| Water/Sodium Hydroxide Mixed 3:1 | 27.1 |
| Coconut Oil | 36.1 |
| Hydrogenated Palm Oil | 11.9 |
| Olive Oil | 2.3 |
| Wheat Germ Oil | 2.3 |
| Canola Oil | 19.6 |
| Honey | 0.4 |
| Citric Acid | 0.2 |
| Lecithin | 0.1 |
| Scent (optional) | Variable |

This embodiment produces a bar of soap which generates a copious lather, and hardens in a short time approximately (2.6 hours) after pouring. In addition, the soap is sufficiently hard to resist premature softening or dissolving, and yet can be used to work up a good lather quickly.

ALTERNATIVE EMBODIMENT NUMBER ONE

| | |
|---|---|
| Caproic Acid | 0.25 |
| Caprylic Acid | 3.4 |
| Capric Acid | 2.4 |
| Lauric Acid | 17.0 |
| Myristic Acid | 6.15 |
| Palmitic Acid | 12.3 |
| Stearic Acid | 4.1 |
| Oleic Acid | 21.1 |
| Linoleic Acid | 3.0 |
| Linolenic Acid | 1.4 |
| Alpha Linoleic Acid | 0.16 |
| Vitamin E | 0.79 |
| Arachidic Acid | 0.17 |
| Water/Sodium Hydroxide Mixed 3:1 | 27.1 |
| Honey | 0.38 |
| Citric Acid | 0.18 |
| Lecithin | 0.09 |

This embodiment is made from a mixture of the following ingredients:

| | |
|---|---|
| Water/Sodium Hydroxide Mixed 3:1 | 27.1 |
| Coconut Oil | 36.1 |
| Hydrogenated Palm Oil | 11.9 |
| Olive oil | 2.3 |
| Wheat Germ oil | 2.3 |
| Palm Oil | 19.6 |
| Honey | 0.4 |
| Citric Acid | 0.2 |
| Lecithin | 0.1 |
| Scent | Variable |

This embodiment produces a superior bar of a pale cream colour which gives a rapid, copious lather.

ALTERNATIVE EMBODIMENT NUMBER TWO

| | |
|---|---|
| Caproic Acid | 0.25 |
| Caprylic Acid | 3.4 |
| Capric Acid | 2.4 |
| Lauric Acid | 16.9 |
| Myristic Acid | 6.0 |
| Palmitic Acid | 4.2–4.5 |
| Stearic Acid | 3.5–3.6 |
| Oleic Acid | 24.3–25.5 |
| Linoleic Acid | 44.8–5.7 |
| Linolenic Acid | 3.0–4.0 |
| Palmitoleic Acid | 0.04–0.06 |
| Erucic Acid | 0.04–0.35 |
| Alpha Linoleic Acid | 0.16 |
| Vitamin E | 0.79 |
| Arachidic Acid | 0.11 |
| Water/Sodium Hydroxide Mixed 3:1 | 27.1 |
| Honey | 0.38 |
| Citric Acid | 0.18 |
| Lecithin | 0.09 |

This embodiment is made from a mixture of the following ingredients:

| | |
|---|---|
| Water/Sodium Hydroxide Mixed 3:1 | 27.1 |
| Coconut Oil | 36.1 |
| Hydrogenated Palm Oil | 11.9 |
| Olive oil | 2.3 |
| Wheat Germ oil | 2.3 |
| Canola Oil | 19.6 |
| Honey | 0.4 |
| Citric Acid | 0.2 |
| Lecithin | 0.1 |
| Scent | Variable |

This embodiment produces a hard bar of an ivory colour with slightly less satisfactory lather.

ALTERNATIVE EMBODIMENT NUMBER THREE

| | |
|---|---|
| Caproic Acid | 0.25 |
| Caprylic Acid | 3.4 |
| Capric Acid | 2.4 |
| Lauric Acid | 17.0 |
| Myristic Acid | 6.2 |
| Palmitic Acid | 18.4 |
| Stearic Acid | 5.9 |
| Oleic Acid | 13.2 |
| Linoleic Acid | 3.0 |
| Linolenic Acid | 1.3 |
| Alpha Linoleic Acid | 0.16 |
| Vitamin E | 0.79 |
| Arachidic Acid | 0.17 |
| Water/Sodium Hydroxide Mixed 3:1 | 27.1 |
| Honey | 0.38 |
| Citric Acid | 0.18 |
| Lecithin | 0.09 |

This embodiment is made from a mixture of the following ingredients:

| | |
|---|---|
| Water/Sodium Hydroxide Mixed 3:1 | 27.1 |
| Coconut Oil | 36.1 |
| Hydrogenated Palm Oil | 11.9 |
| Olive Oil | 2.3 |
| Wheat Germ Oil | 2.3 |
| Palm Oil | 19.6 |
| Honey | 0.4 |
| Citric Acid | 0.2 |
| Lecithin | 0.1 |
| Scent | Variable |

This embodiment produces a hard bar of darker ivory colour with satisfactory lather, slightly less than alternative embodiment number one.

ALTERNATIVE EMBODIMENT NUMBER FOUR

| | |
|---|---|
| Caproic Acid | 0.13 |
| Caprylic Acid | 1.7 |
| Capric Acid | 1.2 |
| Lauric Acid | 8.5 |
| Myristic Acid | 3.4 |
| Palmitic Acid | 19.8 |
| Stearic Acid | 2.1 |
| Oleic Acid | 18.5 |
| Linoleic Acid | 11.4 |
| Linolenic Acid | 4.9 |
| Palmitoleic Acid | 0.36 |
| Alpha Linoleic Acid | 0.02 |
| Vitamin E | 0.13 |
| Arachidic Acid | 0.12 |

| | |
|---|---|
| Water/Sodium Hydroxide Mixed 3:1 | 27.1 |
| Honey | 0.38 |
| Citric Acid | 0.18 |
| Lecithin | 0.09 |

This embodiment is made from a mixture of the following ingredients:

| | |
|---|---|
| Water/Sodium Hydroxide Mixed 3:1 | 27.1 |
| Coconut Oil | 18.1 |
| Hydrogenated Palm Oil | 11.9 |
| Olive Oil | 0.4 |
| Wheat Germ Oil | 0.4 |
| Palm Oil | 41.4 |
| Honey | 0.4 |
| Citric Acid | 0.2 |
| Lecithin | 0.1 |
| Scent | Variable |

This embodiment produces a bar that is less than satisfactory. It takes 4–21 days to harden.

ALTERNATIVE EMBODIMENT NUMBER FIVE

| | |
|---|---|
| Caproic Acid | 0.13 |
| Caprylic Acid | 1.7 |
| Capric Acid | 1.2 |
| Lauric Acid | 8.5 |
| Myristic Acid | 3.4 |
| Palmitic Acid | 17.9 |
| Stearic Acid | 6.1 |
| Oleic Acid | 28.6 |
| Linoleic Acid | 4.1 |
| Linolenic Acid | 0.3 |
| Alpha Linoleic Acid | 0.03 |
| Vitamin E | 0.1 |
| Arachidic Acid | 0.2 |
| Water/Sodium Hydroxide Mixed 3:1 | 27.1 |
| Honey | 0.38 |
| Citric Acid | 0.18 |
| Lecithin | 0.09 |

This embodiment is made from a mixture of the following ingredients:

| | |
|---|---|
| Water/Sodium Hydroxide Mixed 3:1 | 27.1 |
| Coconut Oil | 18.1 |
| Hydrogenated Palm Oil | 18.1 |
| Olive Oil | 0.4 |
| Wheat Germ Oil | 0.4 |
| Palm Oil | 35.2 |
| Honey | 0.4 |
| Citric Acid | 0.2 |
| Lecithin | 0.1 |
| Scent | Variable |

This embodiment produces a bar that requires extended time for hardening and that absorbs water more readily during use.

OPERATION OR MIXING PROCEDURE

UTENSILS

Glass or stainless steel mixing containers; plastic, stainless steel or wooden stirring utensils.

Add sodium hydroxide to purified water and stir until clear. Have adequate ventilation and wear protective clothing and rubber gloves. Harmful fumes arise when mixing sodium hydroxide and water and care must be taken not to breathe these fumes. Set mixture aside to cool to temperature of 60°–90° Fahrenheit.

Melt oils in microwave or slowly on stove-top, then measure; set aside to cool to temperature of 60°–100° F.

Slowly add sodium hydroxide/water mixture to oil mixture in a thin stream, stirring constantly. Stirring can be done by hand or on low speed with electric mixer with stainless steel beaters. Stir periodically while thickening. This mixture will take approximately two hours to thicken to a point where it can be poured into moulds. Time will vary from 1 hour to 5 hours depending on temperature of the room, temperature of mixture, and types of oils used. To test for correct thickness two methods can be used: the spoon stands up in the mixture, or when a spoonful is drizzled on top of total mixture, it stays on top and does not immediately mix with the rest of the mixture.

At this point, add honey, citric acid and scent. It is important to add the scent (i.e. perfume oil or essential oil) at this point. If it is included earlier in the process, most of its scent will be lost in the saponification process. Stir very thoroughly and pour into moulds. Soap will be ready to remove from moulds after 3–12 hours.

VARIABLES

If sodium hydroxide/water mixture is added to oils when temperature is too high, saponification time will be greatly increased. If temperature is allowed to get too low, some of the oils will harden and must be melted again.

The separate mixtures can be left overnight before being joined without any ill effects.

Although the cold-process of soap-making is preferred, this recipe can be adapted to any recognized soap manufacturing process.

GENERAL PRINCIPLES

It can be seen from the above embodiments that there is a range of mixtures of different basic ingredients, which produce soaps of particular types. There is a minimum number of different types of oils combined in a minimum percentage of volume as specified on pages 3 and 4 of the present specification.

As specified previously, substitutions of certain oils in the minimum core ingredients is possible and produce acceptable soaps. However, the following ratios must apply to all embodiments:

Ratio of sodium hydroxide to total oils is 1:8.

Ratio of sodium hydroxide to water is 1:3.

These ratios need to be consistent and should have minimal variation. If too much sodium hydroxide is used, a harsh, brittle soap will be achieved. With too little sodium hydroxide, saponification will not be complete and the soap will stay too soft or will have an oily layer on top.

All embodiments described above have primary core ingredients within ranges as specified below.

| | |
|---|---|
| Caproic Acid | 0.125–0.25 |
| Caprylic Acid | 1.7–3.4 |
| Capric Acid | 1.2–2.4 |
| Lauric Acid | 8.5–17.0 |
| Myristic Acid | 3.3–6.2 |
| Palmitic Acid | 4.2–19.8 |
| Stearic Acid | 2.1–6.1 |

-continued

| | |
|---|---|
| Oleic Acid | 13.2–28.6 |
| Linoleic Acid | 3.0–11.4 |
| Linolenic Acid | 0.3–5.0 |
| Alpha Linoleic Acid | 0.025–0.16 |
| Vitamin E | 0.126–0.79 |
| Water/Sodium Hydroxide Mixed 3:1 | 27.10 |
| Honey | 0.38 |
| Citric Acid | 0.18 |
| Lecithin | 0.09 |

These primary core ingredients are found in a mixture of the following ingredients:

| | Preferred Range | Maximum Range |
|---|---|---|
| Water/Sodium Hydroxide Mixed 3:1 | 27.1 | 27–27.2 |
| Coconut Oil | 18.1–36.1 | 15–37 |
| Olive Oil | 0.4–2.3 | 0–3 |
| Wheat Germ Oil | 0.4–2.3 | 0–10 |
| Honey | 0.4 | 0–1 |
| Citric Acid | 0.2 | 0–.4 |
| Lecithin | 0.1 | 0–.2 |
| Scent | Variable | |

In addition, the following secondary ingredients are found in some of the embodiments in the ranges specified below.

| | |
|---|---|
| Palmitoleic Acid | 0–0.059 |
| Erucic Acid | 0–0.35 |
| Arachidic Acid | 0–0.27 |

These secondary core ingredients are found in ranges of the following ingredients.

| | Preferred Range | Maximum Range |
|---|---|---|
| Hydrogenated Palm Oil | 0–11.9 | 0–18 |
| Palm Oil | 0–35.4 | 0–36 |
| Hydrogenated Canola Oil | 0–11.9 | 0–20 |
| Canola Oil | 0–19.6 | 0–36 |

It can be seen that some of the ingredients have a relatively wide range of ratios, and some ingredients are not necessary. The list below summarizes the upper and lower limits of each of the ingredients used in the mixtures, and as detailed above, some substitutions can be used to eliminate some of the ingredients listed, provided other important parameters of the specification are followed.

| MAXIMUM ACCEPTABLE RANGE OF INGREDIENTS | |
|---|---|
| Caproic Acid | 0.10–0.26 |
| Caprylic Acid | 1.41–3.48 |
| Capric Acid | 1.00–2.48 |
| Lauric Acid | 7.0–17.4 |
| Myristic Acid | 2.47–6.7 |
| Palmitic Acid | 1.21–31.7 |
| Stearic Acid | 0.15–14.5 |
| Oleic Acid | 1.3–57.1 |
| Linoleic Acid | 0.31–19.2 |
| Linolenic Acid | 0.01–4.8 |
| Alpha Linoleic Acid | 0.0–0.7 |
| Vitamin E | 0.0–3.6 |
| Water/Sodium Hydroxide Mixed 3:1 | 27.0–27.2 |
| Honey | 0.0–1.0 |
| Citric Acid | 0–0.4 |

-continued

| MAXIMUM ACCEPTABLE RANGE OF INGREDIENTS | |
|---|---|
| Lecithin | 0–0.2 |
| Palmitoleic Acid | 0–0.11 |
| Erucic Acid | 0–0.65 |
| Arachidic Acid | 0–.29 |

SUBSTITUTIONS OF VARIOUS OILS

Palm Oil and Canola Oil can be used interchangeably. Hydrogenated Canola Oil can be substituted for Hydrogenated Palm Oil. If Hydrogenated Canola Oil is used, use regular Palm Oil; if Hydrogenated Palm Oil is used, use regular Canola Oil. Coconut Oil is essential to the conditioning qualities of the soap so should not be varied more than 10%. If using less coconut oil, increase the hydrogenated oil being used to ensure a firm bar. Safflower oil can be substituted for Canola oil, with minimal volume adjustments.

Wheat Germ Oil can comprise anywhere from 0.18% to 4.5% of total oils and still achieve a good bar of soap. The regular canola, palm or substituted oil should be adjusted accordingly. An unattractive coloured bar results with using 4.5% wheat germ oil and hair is left somewhat heavy-feeling, though it is an excellent bar for skin. Using as little as 0.18% will diminish the conditioning qualities of the soap as the Vitamin E content of Wheat Germ Oil is a valuable nutrient for hair and skin.

It is possible to vary the combinations of oils by plus or minus 20% in order to achieve a satisfactory soap.

A good shampoo/conditioner body bar can be obtained using a mixture of all non-hydrogenated oils such as canola, safflower, olive, wheat germ and coconut. The problem that results from this mixture is that it takes from 3–6 weeks to harden and does not harden nicely shaped. The resultant soap is usable and satisfactory for cleansing purposes, but is not aesthetically pleasing and is impractical as it takes such a long time to cure.

VARIABLES IN OTHER INGREDIENTS

Any honey can be used with equal results. Honey can be included in any amount from 0–1%. It has valuable conditioning qualities for skin and hair so leaving it out would detract from conditioning qualities of the soap, and too much leaves a residue on hair that makes it heavy. Adding or subtracting honey does not affect the saponification of the soap.

Citric Acid can be used in powder or liquid form with equal results. The volumes of citric acid stated herein are volumes measured in the powder form. Citric acid is used to regulate pH levels so can be adjusted according to needs.

Lecithin is an anti-oxidant. It can be omitted without affecting saponification of the soap and can be used in quantities of 0.09 to 0.18%.

Scent is optional and can be any scent desired. Perfume oils and essential oils are equally effective and are added in amounts according to personal preference.

I claim:

1. A skin and hair cleansing bar comprising:
   (a) from about 0.10 to about 0.26% volume Caproic Acid
   (b) from about 1.41 to about 3.48% volume Caprylic Acid
   (c) from about 1.00 to about 2.48% volume Capric Acid
   (d) from about 7.0 to about 17.4% volume Lauric Acid (e) from about 2.47 to about 6.7% volume Myristic Acid (f) from about 1.21 to about 31.7% volume Palmitic Acid (g) from about 0.15 to about 14.5% volume Stearic Acid (h) from about 1.3 to about 57.1% volume Oleic Acid (i) from about 0.31 to about 19.2% volume Linoleic Acid (j) from about 0.01 to about 4.8% volume Linolenic Acid; and (k) from about 27.0 to about 27.2% volume Water/Sodium Hydroxide Mixed 3:1.

2. The cleansing bar as described in claim 1 further comprising up to about 0.7% volume Alpha Linoleic Acid.

3. The cleansing bar as described in claim 1 further comprising up to about 3.6% volume Vitamin E.

4. The cleansing bar as described in claim 1 further comprising up to about 1.0% volume Honey.

5. The cleansing bar as described in claim 1 further comprising up to about 0.4% volume Citric Acid.

6. The cleansing bar as described in claim 1 further comprising up to about 0.2% volume Lecithin.

7. The cleansing bar as described in claim 1 further comprising up to about 0.11% volume Palmitoleic Acid.

8. The cleansing bar as described in claim 1 further comprising up to about 0.65% volume Erucic Acid.

9. The cleansing bar as described in claim 1 further comprising up to about 0.29% volume Arachidic Acid.

10. The cleansing bar as described in claim 1 further comprising:

(a) from nil to about 0.7% volume Alpha Linoleic Acid;

(b) from nil to about 3.6% volume Vitamin E;

(c) from nil to about 1.0% volume Honey;

(d) from nil to about 0.4% volume Citric Acid;

(e) from nil to about 0.2% volume Lecithin;

(f) from nil to about 0.11% volume Palmitoleic Acid;

(g) from nil to about 0.65% volume Erucic Acid; and (h) from nil to about 0.29% volume Arachidic Acid.

11. The cleansing bar as described in claim 10 wherein:

(a) the Caproic acid concentration is from about 0.125 to about 0.25% volume;

(b) the Caprylic Acid concentration is from about 1.7 to about 3.39% volume;

(c) the Capric Acid concentration is from about 1.21 to about 2.42% volume;

(d) the Lauric Acid concentration is from about 8.49 to about 17.0% volume;

(e) the Myristic Acid concentration is from about 3.33 to about 6.18% volume;

(f) the Palmitic Acid concentration is from about 4.22 to about 19.76% volume;

(g) the Stearic Acid concentration is from about 2.08 to about 6.11% volume;

(h) the Oleic Acid concentration is from about 13.2 to about 28.6% volume;

(i) the Linoleic Acid concentration is from about 2.96 to about 11.36% volume;

(j) the Linolenic Acid concentration is from about 0.31 to about 5.0% volume;

(k) the Alpha Linoleic Acid concentration is from about 0.025 to about 0.16% volume;

(l) the Vitamin E concentration is from about 0.126 to about 0.79% volume;

(m) the Water/Sodium Hydroxide Mixed 3:1 concentration is about 27.10% volume;

(n) the Honey concentration is about 0.38% volume;

(o) the Citric Acid concentration is about 0.18% volume; and (p) the Lecithin concentration is about 0.09% volume.

12. The cleansing bar of claim 1 wherein the volume percent of ingredients is about:

| Ingredient | Volume % |
| --- | --- |
| Caproic Acid | 0.25 |
| Caprylic Acid | 3.39 |
| Capric Acid | 2.42 |
| Lauric Acid | 16.92 |
| Myristic Acid | 6.15 |
| Palmitic Acid | 12.29 |
| Stearic Acid | 4.13 |
| Oleic Acid | 21.14 |
| Linoleic Acid | 3.04 |
| Linolenic Acid | 1.36 |
| Alpha Linoleic Acid | 0.16 |
| Vitamin E | 0.79 |
| Arachidic Acid | 0.17 |
| Water/Sodium Hydroxide Mixed 3:1 | 27.10 |
| Honey | 0.38 |
| Citric Acid | 0.18 |
| Lecithin | 0.09 |

13. The cleansing bar of claim 1 wherein the volume percent of ingredients is about:

| Ingredient | Volume % |
| --- | --- |
| Caproic Acid | 0.25 |
| Caprylic Acid | 3.39 |
| Capric Acid | 2.42 |
| Lauric Acid | 16.9 |
| Myristic Acid | 5.96 |
| Palmitic Acid | 4.22–4.52 |
| Stearic Acid | 3.52–3.6 |
| Oleic Acid | 24.31–25.49 |
| Linoleic Acid | 44.76–5.74 |
| Linolenic Acid | 2.98–3.98 |
| Palmitoleic Acid | 0.04–0.06 |
| Erucic Acid | 0.04–0.35 |
| Alpha Linoleic Acid | 0.16 |
| Vitamin E | 0.79 |
| Arachidic Acid | 0.11 |
| Water/Sodium Hydroxide Mixed 3:1 | 27.10 |
| Honey | 0.38 |
| Citric Acid | 0.18 |
| Lecithin | 0.09 |

14. The cleansing bar of claim 1 wherein the volume percent of ingredients is about:

| Ingredient | Volume % |
| --- | --- |
| Caproic Acid | 0.25 |
| Caprylic Acid | 3.39 |
| Capric Acid | 2.42 |
| Lauric Acid | 16.99 |
| Myristic Acid | 6.18 |
| Palmitic Acid | 18.44 |
| Stearic Acid | 5.91 |
| Oleic Acid | 13.2 |
| Linoleic Acid | 2.96 |
| Linolenic Acid | 1.32 |
| Alpha Linoleic Acid | 0.16 |
| Vitamin E | 0.79 |
| Arachidic Acid | 0.17 |
| Water/Sodium Hydroxide Mixed 3:1 | 27.10 |

-continued

| Ingredient | Volume % |
|---|---|
| Honey | 0.38 |
| Citric Acid | 0.18 |
| Lecithin | 0.09 |

15. The cleansing bar of claim 1 wherein the volume percent of ingredients is about:

| Ingredient | Volume % |
|---|---|
| Caproic Acid | 0.13 |
| Caprylic Acid | 1.7 |
| Capric Acid | 1.21 |
| Lauric Acid | 8.49 |
| Myristic Acid | 3.39 |
| Palmitic Acid | 19.77 |
| Stearic Acid | 2.08 |
| Oleic Acid | 18.47 |
| Linoleic Acid | 11.37 |
| Linolenic Acid | 4.87 |
| Palmitoleic Acid | 0.36 |
| Alpha Linoleic Acid | 0.02 |
| Vitamin E | 0.13 |
| Arachidic Acid | 0.12 |
| Water/Sodium Hydroxide Mixed 3:1 | 27.10 |
| Honey | 0.38 |
| Citric Acid | 0.18 |
| Lecithin | 0.09 |

16. The cleansing bar of claim 1 wherein the volume percent of ingredients is about:

| Ingredient | Volume % |
|---|---|
| Caproic Acid | 0.13 |
| Caprylic Acid | 1.7 |
| Capric Acid | 1.2 |
| Lauric Acid | 8.49 |
| Myristic Acid | 3.42 |

-continued

| Ingredient | Volume % |
|---|---|
| Palmitic Acid | 17.88 |
| Stearic Acid | 6.1 |
| Oleic Acid | 28.60 |
| Linoleic Acid | 4.1 |
| Linolenic Acid | 0.3 |
| Alpha Linoleic Acid | 0.03 |
| Vitamin E | 0.1 |
| Arachidic Acid | 0.2 |
| Water/Sodium Hydroxide Mixed 3:1 | 27.10 |
| Honey | 0.38 |
| Citric Acid | 0.18 |
| Lecithin | 0.09 |

17. A skin and hair cleansing bar comprising:

| Ingredient | Volume % |
|---|---|
| Water/Sodium Hydroxide Mixed 3:1 | 27.1 |
| Coconut Oil | 18.1–36.1 |
| Olive Oil | 0.4–2.3 |
| Wheat Germ Oil | 0.4–2.3 |
| Honey | 0.04 |
| Citric Acid | 0.02 |
| Lecithin | 0.01 |

18. The bar as described in claim 1, wherein the ratio of sodium hydroxide to total oils is about 1:8 by volume.

19. The bar as described in claim 18, wherein the ratio of sodium hydroxide to water is about 1:3 by volume.

20. The bar as described in claim 1, wherein the ratio of sodium hydroxide to total oils is about 1:8 by volume.

21. The bar as described in claim 20, wherein the ratio of sodium hydroxide to water is about 1:3 by volume.

22. The bar as described in claim 1, wherein the ratio of sodium hydroxide to total oils is about 1:8 by volume.

23. The bar as described in claim 22, wherein the ratio of sodium hydroxide to water is about 1:3 by volume.

* * * * *